US005756827A

United States Patent [19]

Sivik

[11] Patent Number: 5,756,827

[45] Date of Patent: May 26, 1998

[54] MANUFACTURE OF PERFUMES FOR LAUNDRY AND CLEANING COMPOSITIONS

[75] Inventor: Mark Robert Sivik, Fairfield, Ohio

[73] Assignee: The Procter & Gamble Company, Cincinnati, Ohio

[21] Appl. No.: 482,668

[22] Filed: Jul. 7, 1995

Related U.S. Application Data

[63] Continuation-in-part of Ser. No. 277,558, Jul. 19, 1994.

[51] Int. Cl.$^6$ .......... C07C 69/34

[52] U.S. Cl. .......... 560/201

[58] Field of Search .......... 560/201

[56] References Cited

U.S. PATENT DOCUMENTS

| | | | |
|---|---|---|---|
| 2,220,854 | 11/1940 | Slagh | 260/485 |
| 3,077,457 | 2/1963 | Kulka | 252/305 |
| 4,151,357 | 4/1979 | Mishima et al. | 544/386 |
| 4,199,519 | 4/1980 | Mishima et al. | 260/413 |
| 4,440,663 | 4/1984 | Boyer et al. | 252/174.11 |
| 5,298,569 | 3/1994 | Yamamori et al. | 525/329.5 |
| 5,312,950 | 5/1994 | Boaz | 558/51 |

FOREIGN PATENT DOCUMENTS

| | | | |
|---|---|---|---|
| 118611 | 9/1984 | European Pat. Off. . | |
| 397245 | 11/1990 | European Pat. Off. | C11D 3/50 |
| 404470 | 12/1990 | European Pat. Off. | A61K 7/46 |
| 430315 | 6/1991 | European Pat. Off. | C11D 3/386 |
| 1286692 | 1/1969 | Germany . | |
| 50-029877 | 3/1975 | Japan . | |
| 53-018510 | 2/1978 | Japan . | |
| 53-053614 | 5/1978 | Japan . | |
| 64-001799 | 1/1989 | Japan | C11D 3/50 |
| 3-17025 | 1/1991 | Japan | A61K 47/48 |
| 2087885 | 6/1982 | United Kingdom | C07C 69/743 |
| WO 94/13766 | 6/1994 | WIPO | C11B 9/00 |
| WO 95/04809 | 2/1995 | WIPO | C11D 3/50 |

OTHER PUBLICATIONS

Chem Abstracts 71:24728, 1969.

Patent Abstracts of Japan, JP 59001446, Jan. 6, 1984 (Toray).

Derwent Abstract, JP 48043329 (Toray Ind.).

Derwent Abstract, JP 3181599, Aug. 7, 1991 (Lion Corporation).

Derwent Abstract, JP 2034696, Feb. 5, 1990 (Kao Corporation).

Derwent Abstract, JP 59001410, Jan. 6, 1984 (Toray Ind.).

Derwent Abstract, JP 2166195, Jun. 26, 1990 (Lion Corporation).

Derwent Abstract, JP 60023498, Feb. 6, 1985 (Lion Corporation).

Derwent Abstract, JP 63035696, Feb. 16, 1988 (Lion Corporation).

Derwent Abstract, JP 64001799, Jan. 6, 1989 (Kao Corporation).

Cori, Osvaldo, "Rearrangement of Linalool, Geraniol, and Nerol and Their Derivatives", J. Org. Chem. (1986) vol. 51, pp. 1310–1316.

Schmid, *Tetrahedron Letters*, 33, p. 757 (1992).

Carey et al., Advanced Organic Chemistry, Part A, 2nd Ed., pp. 421–426 (Penum, NY; 1984).

Chemical Abstracts Service, Abstract #66(7): 28371h (1967).

Chemical Abstracts Service, Abstract #117(26): 253848k (1992).

Chemical Abstracts Service, Abstract #115(14): 141973Z (1991).

Mukaiyama et al., *Chem. Letters*, pp. 563–566 (1980).

"Geranyl crotonate", *Food Cosmet. Toxicol.*, 1974, 12, p. 891.

"Geranyl phenylacetate", *Food Cosmet. Toxicol.*, 1974, 12, p. 895.

Mohacsi, Erno, "Regioselective Epoxidation of Geranyl Palmitate with Metachloroperbenzoic Acid", *Synthetic Communications*, 21(21), (1991), pp. 2257–2261.

Erdmann, Ernst, "Ueber einige Ester und einen krystallisirten Pseudoester des Rhodinols", *Chem. Ber.*, 31, (1898), pp. 356–360.

Chemical Abstracts Service, Abstract #71:24728, Weitzel (1969).

Larock, R.C., *Comprehensive Organic Transformations*, VCH Publishers, NY; 1989), pp. 966–972, 978–981, 985–987, 989–990, 993–994.

U.S. application No. 08/277,558, Hartman et al., filed Jul. 19, 1994.

U.S. application No. 08/517,941, Hartman et al., filed Aug. 22, 1995.

*Primary Examiner*—Samuel Barts

*Attorney, Agent, or Firm*—Richard S. Echler, Sr.; Brian M. Bolam; Kim W. Zerby

[57] ABSTRACT

A process for manufacturing selected nonionic or anionic esters of allylic alcohols, preferably diesters of allylic perfume alcohols, useful for laundry and cleaning products.

15 Claims, No Drawings

MANUFACTURE OF PERFUMES FOR LAUNDRY AND CLEANING COMPOSITIONS

CROSS REFERENCE TO RELATED APPLICATION

This is a continuation-in-part application of U.S. application Ser. No. 08/277,558, filed Jul. 19, 1994, by Hartman et al.

FIELD OF THE INVENTION

The present invention relates to a process for manufacturing nonionic or anionic esters of allylic alcohol perfumes useful for laundry and cleaning products.

BACKGROUND OF THE INVENTION

Consumer acceptance of cleaning and laundry products is determined not only by the performance achieved with these products but the aesthetics associated therewith. The perfume systems are therefore an important aspect of the successful formulation of such commercial products.

What perfume system to use for a given product is a matter of careful consideration by skilled perfumers. While a wide array of chemicals and ingredients are available to perfumers, considerations such as availability, cost, and compatibility with other components in the compositions limit the practical options. Thus, there continues to be a need for low-cost, compatible perfume materials useful for cleaning and laundry compositions.

It has been discovered that nonionic and anionic esters of certain allylic perfume alcohols are particularly well suited for laundry and cleaning compositions. In particular, it has been discovered that depending on the acid group utilized and/or the laundry/cleaning compositions into which these are incorporated, esters of allylic perfume alcohols will hydrolyze to give one or more of the possible allylic alcohol perfumes. In addition, slowly hydrolyzable esters of allylic perfume alcohols provide release of the perfume over a longer period of time than by the use of the perfume itself in the laundry/cleaning compositions. Such materials therefore provide perfumers with more options for perfume ingredients and more flexibility in formulation considerations.

Important for the commercial applicability of these materials is the ability to manufacture these esters by processes that are inexpensive, high yielding and easy to control. These and other advantages of the present invention will be seen from the disclosures hereinafter.

BACKGROUND ART

Mechanistic studies are described in Schmid, *Tetrahedron Letters,* 33, p. 757 (1992); and Cori et al., *J. Org. Chem.,* 51, p. 1310 (1986). Carey et al., *Advanced Organic Chemistry, Part A,* 2nd Ed., pp. 421–426 (Plenum, N.Y.; 1984) describes ester chemistry more generally.

General methods for manufacturing esters are taught in Larock, R. C., *Comprehensive Organic Transformations,* pp. 966–972, 978–981, 985–987, 989–990 and 993–994 (VCH Publishers, N.Y.; 1989).

Compositions of fragrance materials (having certain values for Odour Intensity Index, Malodour Reduction Value and Odour Reduction Value) said to be used as fragrance compositions in detergent compositions and fabric conditioning compositions are described in European Patent Application Publication No. 404,470, published Dec. 27, 1990 by Unilever PLC. Example 1 describes a fabric-washing composition containing 0.2% by weight of a fragrance composition which itself contains 4.0% geranyl phenylacetate.

See also WO 95/04809, published Feb. 16, 1995, by Firmenich, relating to a method for scenting fabrics being washed in the presence of a lipase-containing detergent, optionally followed by a fabric softener, wherein the compositions contain selected ester, aldehyde or ketone derivatives.

SUMMARY OF THE INVENTION

The present invention relates to a process for manufacturing esters of allylic alcohols, preferably succinate diesters of an allylic alcohol perfume, having the formula:

$$CR'''_2{=}CR''{-}CR'_2{-}OC(O){-}CR_2CR_2{-}C(O)O{-}R^1$$

wherein R, $R^1$, R', R'', and R''' are as described hereinafter, said process comprising the step of reacting an allylic alcohol having the formula:

$$CR'''_2{=}CR''{-}CR'_2{-}OH$$

with a carboxylic acid anhydride having the formula:

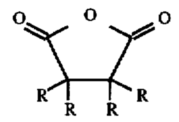

wherein said reaction is conducted at a temperature above about 60° C., preferably above about 130° C., in the absence of a metal or strong acid catalyst which isomerizes the allylic alcohol.

Preferred processes comprise the steps of:

(a) reacting an allylic alcohol and carboxylic acid anhydride as described hereinbefore at a temperature within the range of from about 60° C. to about 240° C., preferably within the range of from about 70° C. to about 180° C., and more preferably from about 130° C. to about 165° C., in the absence of a metal or strong acid catalyst which isomerizes the allylic alcohol, and wherein further the molar ratio of allylic alcohol to anhydride is at least about 1:1 (preferably at least 1.5:1);

(b) optionally removing any excess allylic alcohol from the ester;

(c) optionally removing insoluble matter (e.g., succinic acid by filtration); and (d) collecting the ester.

R are independently selected from the group consisting of $C_1$–$C_{30}$, preferably hydrogen $C_1$–$C_{20}$, straight, branched or cyclic allyl, alkenyl, alkynyl, alkylaryl, or aryl group, or two R moieties are connected to form a cycloalkyl chain. Preferred are at least two R being hydrogen, preferably three R being hydrogen, and most preferred is all R being hydrogen (i.e., succinic anhydride).

$R^1$ is selected from the group consisting of hydrogen, a cationic M moiety, and the moiety $CR'''_2{=}CR''{-}CR'_2{-}$, wherein M is a cationic moiety capable of forming a salt of a carboxylic acid moiety (e.g., alkali and alkaline metals such as sodium and potassium, as well as quaternary ammonium moieties). Preferred $R^1$ is a $CR'''_2{=}CR''{-}CR'_2{-}$ moiety, which may be the same (preferred) or different moiety from the other ester moiety attached to the molecule.

Each R' is independently selected from the group consisting of hydrogen, or a $C_1$–$C_{25}$ straight, branched or cyclic alkyl, alkenyl, alkynyl, alkylaryl, or aryl group. The two R' moieties may be the same or different. Preferably one R' is hydrogen. More preferably, both R' moieties are hydrogen.

R" is selected from the group consisting of hydrogen, or a $C_1$–$C_{25}$ straight, branched or cyclic alkyl, alkenyl, alkynyl, alkylaryl, or aryl group. Preferably, R" is hydrogen.

Each R"' is independently selected from the group consisting of hydrogen, or a $C_1$–$C_{25}$ straight, branched or cyclic alkyl, alkenyl, alkynyl, alkylaryl, or aryl group. The R"' may be the same or different. Preferably, one R"' is hydrogen or a straight, branched or cyclic $C_1$–$C_{20}$ alkyl, alkenyl or alkylaryl groups. More preferably, one R"' is hydrogen, methyl, or ethyl, and the other R"' is a straight, branched or cyclic $C_1$–$C_{20}$ alkyl, alkenyl or alkylaryl group. More preferably, one R"' is a straight, branched or cyclic $C_1$–$C_{15}$ alkyl, alkenyl or alkylaryl group.

In the most preferred embodiment, R' and R" are hydrogen, one R"' is hydrogen, methyl, or ethyl, and the other R"' is a straight, branched or cyclic $C_1$–$C_{20}$ alkyl, alkenyl, or alkylaryl group.

Those skilled in the art will recognize that structural isomers of the above structure are possible. Specifically, cis/trans (also referred to as Z/E) isomers at the double bond in the structure shown above are possible.

Those skilled in the art will also recognize that stereoisomers of the above structure are possible. Specifically, when the two R' groups are different from one another stereoisomers referred to as "R/S" are possible. Again, all possible steroisomers are included within the above present invention structure.

In addition, each of the above R, $R^1$, R', R", and R"' moieties may be unsubstituted or substituted with one or more nonionic and/or anionic substituents. Such substituents may include, for example, halogens, nitro, carboxy, carbonyl, sulfate, sulfonate, hydroxy, and alkoxy, and mixtures thereof.

Preferred laundry and cleaning compositions comprise the esters of geraniol and/or nerol. Geraniol and nerol are trans/cis structural isomers (at the 2,3 position double bond) of the molecules having the formula $HO—CH_2—CH=C(CH_3)—CH_2—CH_2—CH=C(CH_3)_2$. Additional allylic alcohols useful for preparing esters, preferably succinate diesters, according to the present invention are farnesol, cinnamic alcohol and nerolidol.

The most preferred ester prepared by the present invention process is:

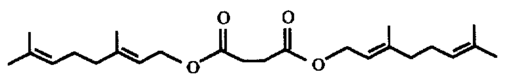

referred to herein as "digeranyl succinate", as well as the neryl ester corresponding to this geranyl ester, including the mixed geranyl neryl succinate ester, and especially mixtures of the corresponding geranyl and neryl esters.

All percentages, ratios and proportions herein are by weight, unless otherwise specified. All documents cited are, in relevant part, incorporated herein by reference.

DETAILED DESCRIPTION OF THE INVENTION (a) Esterification Step

The present invention relates to a process for manufacturing esters of allylic alcohols, preferably succinate diesters of an allylic alcohol perfume, having the formula:

$$CR'''_2{=}CR''—CR'_2—OC(O)—CR_2CR_2—C(O)O—R^1$$

preferably diesters of the formula:

$$CR'''_2{=}CR''—CR'_2—OC(O)—CR_2CR_2—C(O)O—CR'_2—CR''{=}CR'''_2$$

wherein R, R', R", and R"' are as described hereinbefore, said process comprising the step of reacting an allylic alcohol having the formula:

$$CR'''_2{=}CR''—CR'_2—OH$$

with a carboxylic acid anhydride having the formula:

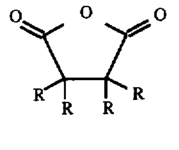

wherein said reaction is conducted at a temperature above about 60° C. in the absence of a metal or strong acid catalyst which isomerizes the allylic alcohol. Again, these esters are preferably formulated such that at least one of the possible alcohol materials obtained upon hydrolysis of the ester is a perfume material.

By the term "strong acid catalyst" is meant any acid more acidic than carboxylic acids, for example para-toluenesulfonic acid, sulfuric acid, and hydrochloric acid. It is necessary for the present invention process to avoid the presence of metals and strong acid catalysts which isomerize the allylic alcohol reactant, since isomerization produces the unwanted allylic alcohol reactant in which the double bond is at the end of the chain and the hydroxyl group is not. Inclusion of these catalysts in the process result in reduced yields of pure diester product, possibly due to rearrangement of the allylic alcohol during the reaction step. Thus, while typically such materials are desired for use in the manufacture of esters to provide the benefits of reduced reaction temperatures and/or time of reaction, they are detrimental to the present process.

Allylic alcohols include farnesol, cinnamic alcohol, nerolidol, geraniol, and nerol. Preferred are geraniol, neryl, and mixtures thereof. Preferred allylic alcohols contain less than about 10 mole percent of water, and preferably are essentially water free. If necessary, the present invention reaction process is preceded by a step of drying the allylic alcohol to reduce the water content therein.

The geranyl and neryl esters are preferred in light of the fact that, depending on the acid moiety present in the ester compound and the use conditions, this ester can provide either a geraniol, nerol or linalool alcohol perfume, or mixtures thereof upon hydrolysis.

The reaction conditions for the present invention process are: preferably the reaction mixture is heated to a temperature within from about 60° C. to about 240° C., preferably within the range of from about 70° C. to about 180° C., and more preferably from about 130° C. to about 165° C.; reaction times are preferably from about 1 hour to about 36 hours, preferably within the range of from about 2 hours to about 24 hours, and more preferably from about 3 hours to about 18 hours; and preferably the allylic alcohol is used relative to the anhydride at a level of at least about 1:1 (moles alcohol to moles anhydride), more preferably at least about 1.5:1, still more preferably at least about 2.0:1, and most preferably in excess of at least about 2.5:1. Preferred ranges for the molar ratio of allylic alcohol to anhydride are within from about 1:1 to about 4:1, more preferably from about 1.5:1 to about 3.5:1, still more preferably from about 2:1 to about 3.5:1, and most preferably from about 2.5:1 to about 3.1:1. Use of excess alcohol is preferred since the excess alcohol acts as a solvent for the reaction mixture, but the presence of solvent is permitted.

During the reaction, it is important to conduct the reaction such that the water produced is effectively removed. This may be accomplished by either conducting the reaction at a temperature about 100° C. while purging the reaction vessel with an inert gas (e.g., nitrogen or argon), or by refluxing the system under inert gas purge if a solvent is present, including the use of solvents capable of azeotoping the water from the reaction vessel, or at reduced pressure.

(b) Methods for Removing Excess Allylic Alcohol

In some applications, it is desirable to remove the excess allylic alcohol from the reaction product to a level of less than about 10%, more preferably less than about 5%, even more preferably less than about 3%.

A number of common procedures can be used to remove the excess allylic alcohol from the reaction product, including:

1) Distillation—either by heating the reaction vessel above the boiling point of the allylic alcohol, or more preferably by applying a partial vacuum to the system and heating more gently, at more than about 50° C. below the boiling point of the allylic alcohol at atmospheric pressure.

2) Use of a Kugelrohr oven—after completion of the reaction, the reaction product is cooled to room temperature and placed in a Kugelrohr oven at about 50°–100° C. for 2–10 hours under high vacuum until the desired amount of allylic alcohol has been removed.

3) Use of a wipe (thin) film evaporator—This method is similar to a simple distillation but is faster due to use of thin film evaporator. Preferred methods involve adding crude reaction product to the evaporator under high vacuum. An advantage of this method is that it can be operated in a continuous mode versus batch mode. A further advantage is that it avoids overheating of the sample which can result in undesirable off-odors and discoloration.

Depending upon the desired level of residual allylic alcohol in the reaction product, the conditions (time, temperature) used in these methods may be adjusted.

Those skilled in the art will recognize that a number of other methods may be used to remove excess allylic alcohol. The examples above are for illustration and are not meant to limit the scope of the invention.

(c) Optional Filtration Step

In some applications it is desirable to further purify the reaction product to remove any insoluble particulate matter. This may be accomplished, for example, by simple gravity filtration of the product under ambient conditions.

(d) Collection of Diester Product

Diester product is preferably collected and stored under a blanket of inert gas, preferably dry nitrogen, to ensure storage stability of the material and to minimize decomposition of the sample due to moisture or oxygen.

The diesters produced by the present invention process are particularly useful in laundry and cleaning products, which are typically used for laundering fabrics and cleaning hard surfaces such as dishware and other surfaces in need of cleaning and/or disinfecting.

The following examples illustrate the present invention process, and compositions which comprise the diesters produced thereby, but are not intended to be limiting thereof.

EXAMPLE I

Digeranyl Succinate

Synthesis (a): A mixture of geraniol and nerol (approximately 70:30 by weight) in the amount of 50.00 g (0.324 mol) and succinic anhydride in the amount of 16.22 g (0.162 mol) are combined with 100 mL of toluene. The mixture is heated to reflux for 18 h at which time the theoretical amount of water is collected. The product mixture is concentrated first by rotary evaporation, and then by Kugelrohr distillation, to give a light yellow oil. Purification of the product by column chromatography provides a colorless oil. Purity of the product is determined by thin layer chromatography and the structure confirmed by $^{13}C$ and $^{1}H$ NMR.

Synthesis (b): A mixture of geraniol and nerol (approximately 70:30 by weight) in the amount of 94.86 g (0.615 mol) and succinic anhydride in the amount of 20.51 g (0.205 mol) are combined at room temperature. The mixture is heated to 140° C. for 6 h while water is removed using an argon sparge. After cooling to room temperature, the mixture is placed in a Kugelrohr oven and concentrated at 80°–85° C. for 5.5 h. Purity of the product is determined by thin layer chromatography and the structure confirmed by $^{13}C$ and $^{1}H$ NMR.

Synthesis (c): In a 22 L three-necked round-bottomed flask fitted with a distillation head and condenser, argon inlet, reflux condenser, internal thermometer, and mechanical stirrer are placed succinic anhydride (2000.0 g, 20 mol, Aldrich) and geraniol (9240.0 g, 60.0 mol, Bush Boake Allen). The mixture is gradually heated to 140°–145° C. letting water distill with argon sweeping over the reaction mixture. After stirring overnight, 310 mL of water is collected (theoretical: 360 mL). Analysis by $^{13}C$ NMR indicates that monoester remains in the mixture. The mixture is reheated to 165° C. for 3 hours at which time no monoester is detected by TLC. The reaction mixture is cooled and then distilled on a Pope wipe-film evaporator at 90° C. (0.03 mm Hg). The diester is isolated as a light yellow oil.

Similar results can be achieved for these synthesis methods by starting with pure geraniol, pure nerol, or other mixtures thereof (e.g., 60:40 geraniol:nerol).

EXAMPLE II

Liquid fabric softener compositions are formulated as follows:

| Ingredient | A Wt. % | B Wt. % | C Wt. % | D Wt. % | E Wt. % |
|---|---|---|---|---|---|
| DEQA (1) | 26.0 | 26.0 | 26.0 | 26.0 | 26.0 |
| Ethanol | 4.2 | 4.2 | 4.2 | 4.2 | 4.2 |
| HCl | 0.01 | 0.01 | 0.01 | 0.01 | 0.01 |
| $CaCl_2$ | 0.46 | 0.46 | 0.46 | 0.46 | 0.46 |
| Silicone Antifoam (2) | 0.15 | 0.15 | 0.15 | 0.15 | 0.15 |
| Preservative (3) | 0.0003 | 0.0003 | 0.0003 | 0.0003 | 0.0003 |
| Perfume | 1.20 | 1.35 | — | 1.35 | 1.20 |
| Digeranyl Succinate (4) | 0.76 | 0.76 | 0.76 | 0.76 | 0.76 |
| Water | 67.22 | 67.07 | 68.08 | 66.73 | 66.78 |

(1) Di-(soft-tallowyloxyethyl) dimethyl ammonium chloride
(2) DC-2310, sold by Dow-Corning
(3) Kathon CG, sold by Rohm & Haas
(4) 1,4-Butandioic acid, 3,7-dimethyl-2,6-octadienyl ester

EXAMPLE III

Additional liquid fabric conditioner formulas include the following.

| Ingredient | F Wt. % | G Wt. % | H Wt. % | I Wt. % | J Wt. % |
|---|---|---|---|---|---|
| DEQA (5) | 5.40 | 18.16 | 18.16 | 22.7 | 22.7 |
| Poly(glycerol monostearate) | 0.83 | 2.40 | 2.40 | 3.00 | 3.00 |
| Tallow Alcohol Ethoxylate-25 | 0.36 | 1.20 | 1.20 | 1.50 | 1.50 |
| HCl | 0.02 | 0.02 | 0.02 | 0.02 | 0.02 |
| $CaCl_2$ | — | 0.20 | 0.20 | 0.30 | 0.30 |
| Silicone Anti-foam | — | 0.019 | 0.019 | 0.019 | 0.019 |
| Soil Release Polymer | — | 0.19 | 0.19 | 0.19 | 0.19 |
| Perfume | 0.187 | 0.70 | 0.70 | 0.90 | 0.90 |
| Blue Dye | 0.002 | 0.005 | 0.005 | 0.006 | 0.006 |
| Digeranyl Succinate (4) | 0.095 | 0.35 | 0.45 | 0.45 | 0.35 |
| Water | 93.11 | 74.34 | 74.24 | 70.92 | 71.02 |

(4) 1,4-Butandioic acid 3,7-dimethyl-2,6-octadienyl ester
(5) Di-(tallowloxyethyl) dimethyl amonium chloride

EXAMPLE IV

Additional dryer added fabric conditioner formulas include the following.

| Component | K Wt. % | L Wt. % | M Wt. % | N Wt. % | O Wt. % |
|---|---|---|---|---|---|
| DEQA (13) | 39.16 | 34.79 | — | — | — |
| DEQA (14) | — | — | 51.81 | — | — |
| DTDMAMS (15) | — | — | — | 20.64 | 25.94 |
| Co-Softener (16) | 54.41 | 40.16 | 27.33 | 33.04 | 41.52 |
| Glycosperse S-20 (17) | — | — | 15.38 | — | — |
| Glycerol Monostearate | — | — | | 20.87 | 26.23 |
| Perfume | 1.61 | 1.65 | 1.52 | 1.61 | 1.21 |
| Perfume/Cyclodextrin Complex | — | 18.88 | — | 19.13 | — |
| Digeranyl Succinate (4) | 0.80 | 0.50 | 0.80 | 0.80 | 1.20 |
| Clay (18) | 4.02 | 4.02 | 3.16 | 3.91 | 3.90 |

(4) 1,4-Butandioic acid, 3,7-dimethyl-2,6-octadienyl ester
(13) Di-(oleyloxyethyl) dimethyl ammonium methylsulfate
(14) Di-(soft-tallowyloxyethyl) hydroxyethyl methyl ammonium methylsulfate
(15) Ditallow dimethyl ammonium methylsulfate
(16) 1:2 Ratio of stearyldimethyl amine:triple-pressed stearic acid
(17) Polyethoxylated sorbitan monostearate, available from Lonza
(18) Calcium Bentonite Clay, Bentonite L, sold by Southern Clay Products

EXAMPLE V

A fabric conditioner bar is prepared having the following components.

| Component | Wt. % |
|---|---|
| Co-Softener (16) | 70.00 |
| Neodol 45-13 (19) | 13.00 |
| Ethanol | 1.00 |
| Dye | 0.01 |
| Perfume | 0.75 |
| Digeranyl Succinate (4) | 0.38 |
| Water | 14.86 |

(4) 1,4-Butandioic acid, 3,7-dimethyl-2,6-octadienyl ester
(16) 1:2 Ratio of stearyldimethyl amine:triple-pressed stearic acid
(19) $C_{14}$–$C_{15}$ linear primary alcohol ethoxylate, sold by Shell Chemical Co.

What is claimed is:

1. A process for manufacturing esters of allylic alcohols having the formula:

$$CR'''_2{=}CR''{-}CR'_2{-}OC(O){-}CR_2CR_2{-}C(O)O{-}R^1$$

said process comprising the steps of:

a) reacting an allylic alcohol having the formula:

$$CR'''_2{=}CR''{-}CR'_2{-}OH$$

with a carboxylic acid anhydride having the formula:

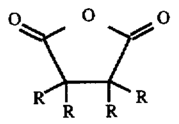

wherein said reaction is conducted at a temperature above about 60° C. in the absence of a metal or strong acid catalyst which isomerizes the allylic alcohol, and wherein further the molar ratio of allylic alcohol to anhydride is at least about 1:1;

b) optionally removing any excess allylic alcohol from the ester;

c) optionally removing insoluble matter; and d) collecting the ester having the formula:

$$CR'''_2{=}CR''{-}CR'_2{-}OC(O){-}CR_2CR_2{-}C(O)O{-}R^1;$$

and wherein each R is independently selected from the group consisting of hydrogen, $C_1$–$C_{30}$, straight, branched or cyclic alkyl, alkenyl, alkynyl, alkylaryl, or aryl group, or two R moieties are connected to form a cycloalkyl chain; $R^1$ is selected from the group consisting of hydrogen, and the moiety $CR'''_2{=}CR''{-}CR'_2{-}$, wherein each of R', R", and R''' is independently selected from the group consisting of hydrogen, or a nonionic or anionic substituted or unsubstituted $C_1$–$C_{25}$ straight, branched or cyclic alkyl, alkenyl, alkynyl, alkylaryl, or aryl group.

2. The process according to claim 1 wherein at least two R of the anhydride formula are hydrogen.

3. The process according to claim 1 wherein the allylic alcohol has the formula wherein at least one R' is hydrogen, R" is hydrogen, and R''' is a straight, branched or cyclic $C_1$–$C_{20}$ alkyl, alkenyl, or alkylaryl group.

4. The process according to claim 1 wherein the reaction is conducted at a temperature within the range of from about 70° C. to about 180° C., and the ratio of allylic alcohol to anhydride is at least about 1.5:1.

5. The process according to claim 2 wherein the reaction is conducted at a temperature within the range of from about 70° C. to about 180° C., and the ratio of allylic alcohol to anhydride is at least about 1.5:1.

6. The process according to claim 5 wherein the allylic alcohol is selected from the group consisting of farnesol, cinnamic alcohol, nerolidol, geraniol, and nerol.

7. A process for manufacturing esters of allylic alcohols having the formula:

$$CR'''_2{=}CR''{-}CR'_2{-}OC(O){-}CH_2CH_2{-}C(O)O{-}R^1$$

said process comprising the steps of:

a) reacting an allylic alcohol having the formula:

$$CR'''_2{=}CR''{-}CR'_2{-}OH$$

with succinic anhydride, wherein said reaction is conducted at a temperature above about 60° C. in the absence of a metal or strong acid catalyst which isomerizes the allylic alcohol, and wherein further the molar ratio of allylic alcohol to anhydride is at least about 1:1;

b) optionally removing any excess allylic alcohol from the ester;

c) optionally removing insoluble matter; and d) collecting the ester which comprises succinate diester; and wherein $R^1$ is selected from the group consisting of hydrogen, and the moiety $CR'''_2=CR''—CR'_2—$, wherein each of R', R", and R"' is independently selected from the group consisting of hydrogen, or a nonionic or anionic substituted or unsubstituted $C_1$–$C_{25}$ straight, branched or cyclic alkyl, alkenyl, alkynyl, alkylaryl, or aryl group.

8. The process according to claim 7 wherein the allylic alcohol has the formula wherein at least one R' is hydrogen, R" is hydrogen, and R"' is a straight, branched or cyclic $C_1$–$C_{20}$ alkyl, alkenyl, or alkylaryl group.

9. The process according to claim 7 wherein the allylic alcohol is selected from the group consisting of farnesol, cinnamic alcohol, nerolidol, geraniol, and nerol.

10. The process according to claim 7 wherein the reaction is conducted at a temperature within the range of from about 70° C. to about 180° C., and the ratio of allylic alcohol to anhydride is at least about 1.5:1.

11. The process according to claim 8 wherein the reaction is conducted at a temperature within the range of from about 70° C. to about 180° C., and the ratio of allylic alcohol to anhydride is within the range of from about 1.5:1 to about 3.5:1.

12. A process for manufacturing esters of allylic alcohols, said process comprising the steps of:

a) reacting an allylic alcohol selected from the group consisting of geraniol, nerol, and mixtures thereof with succinic anhydride, wherein said reaction is conducted at a temperature within the range of from about 60° C. to about 240° C. in the absence of a metal or strong acid catalyst which isomerizes the allylic alcohol, and wherein further the molar ratio of allylic alcohol to anhydride is at least about 1:1;

b) optionally removing any excess allylic alcohol from the ester;

c) optionally removing insoluble matter; and d) collecting the allylic alcohol esters.

13. The process according to claim 12 wherein the reaction is conducted at a temperature within the range of from about 70° C. to about 180° C., and the ratio of allylic alcohol to anhydride is at least 1.5:1.

14. The process according to claim 12 wherein the reaction is conducted at a temperature within the range of from about 70° C. to about 180° C., and the ratio of allylic alcohol to anhydride is within the range of from about 1.5:1 to about 3.5:1.

15. The process according to claim 12 wherein the reaction is conducted at a temperature within the range of from about 130° C. to about 165° C., and the ratio of allylic alcohol to anhydride is within the range of from about 2.5:1 to about 3.1:1.

* * * * *